(12) United States Patent
Umfer

(10) Patent No.: US 11,561,154 B2
(45) Date of Patent: *Jan. 24, 2023

(54) METHOD AND DEVICE FOR MEASURING AN OXYGEN CONTENT OF A HEADSPACE GAS IN A BEVERAGE CAN

(71) Applicant: ANTON PAAR GMBH, Graz-Strassgang (AT)

(72) Inventor: Christof Umfer, Graz (AT)

(73) Assignee: Anton Paar GmbH, Graz-Strassgang (AT)

( * ) Notice: Subject to any disclaimer, the term of this patent is extended or adjusted under 35 U.S.C. 154(b) by 347 days.

This patent is subject to a terminal disclaimer.

(21) Appl. No.: 16/841,874

(22) Filed: Apr. 7, 2020

(65) Prior Publication Data

US 2020/0326263 A1 Oct. 15, 2020

(30) Foreign Application Priority Data

Apr. 12, 2019 (AT) .............................. A 50337/2019

(51) Int. Cl.
  *G01N 33/14* (2006.01)
  *G01N 33/00* (2006.01)
  (Continued)

(52) U.S. Cl.
  CPC ........ *G01N 1/2226* (2013.01); *G01L 19/0092* (2013.01); *G01N 21/6428* (2013.01);
  (Continued)

(58) Field of Classification Search
  CPC .............. G01L 19/0092; G01N 1/2226; G01N 2001/2229; G01N 2021/6432;
  (Continued)

(56) References Cited

U.S. PATENT DOCUMENTS 3,203,248 A * 8/1965 Stutler .................. G01N 30/06
                                                 73/864.34
3,849,070 A * 11/1974 Garza .................... G01N 33/02
                                                 422/68.1
(Continued)

FOREIGN PATENT DOCUMENTS

EP 0567782 A1 11/1993
EP 1887344 A1 2/2008
(Continued)

*Primary Examiner* — Maureen Wallenhorst
(74) *Attorney, Agent, or Firm* — Laurence A. Greenberg; Werner H. Stemer; Ralph E. Locher

(57) ABSTRACT

A method and a device for measuring an oxygen content of a headspace gas in a beverage can. The beverage can is oriented upside down to allow the headspace gas to collect at the bottom. A hollow piercer on a piercing head forms a sampling opening in the bottom of the can through which the sampling tube penetrates. The liquid level in the beverage can is lowered to establish a direct connection of the gas-filled headspace and the sampling opening. Then the headspace gas is transported from the headspace to a sensor unit via the sampling tube and/or the hollow piercer or the piercing head. The oxygen content and/or an oxygen partial pressure and/or a headspace volume of the headspace gas are determined by the sensor unit. The sampling opening is closed off airtight by sealing elements arranged on the piercer or the piercing head.

20 Claims, 1 Drawing Sheet

(51) Int. Cl.
*G01N 1/22* (2006.01)
*G01N 21/64* (2006.01)
*G01L 19/00* (2006.01)

(52) U.S. Cl.
CPC ......... *G01N 33/0036* (2013.01); *G01N 33/14* (2013.01); *G01N 33/143* (2013.01); *G01N 33/146* (2013.01); *G01N 2001/2229* (2013.01); *G01N 2021/6432* (2013.01)

(58) Field of Classification Search
CPC ............ G01N 21/643; G01N 21/6428; G01N 33/0036; G01N 33/14; G01N 33/143; G01N 33/146
USPC ......... 436/20, 148, 150, 127, 136, 138, 164, 436/172, 181; 422/82.01, 82.05, 82.08, 422/82.12, 82.13, 83, 98
See application file for complete search history.

(56) References Cited

U.S. PATENT DOCUMENTS

| | | | | |
|---|---|---|---|---|
| 4,926,681 A | * | 5/1990 | Fitzpatrick | ........... G01N 1/2226 73/52 |
| 5,220,513 A | * | 6/1993 | Seiden | ................... G01N 33/14 73/19.01 |
| 5,363,707 A | | 11/1994 | Augenblick et al. | |
| 7,736,590 B2 | | 6/2010 | Matsuda et al. | |
| 8,408,043 B2 | | 4/2013 | Stehle et al. | |

FOREIGN PATENT DOCUMENTS

| | | |
|---|---|---|
| JP | H04315943 A | 11/1992 |
| JP | H1010020 A | 1/1998 |
| JP | H10104135 A | 4/1998 |
| WO | 2009050530 A1 | 4/2009 |

* cited by examiner

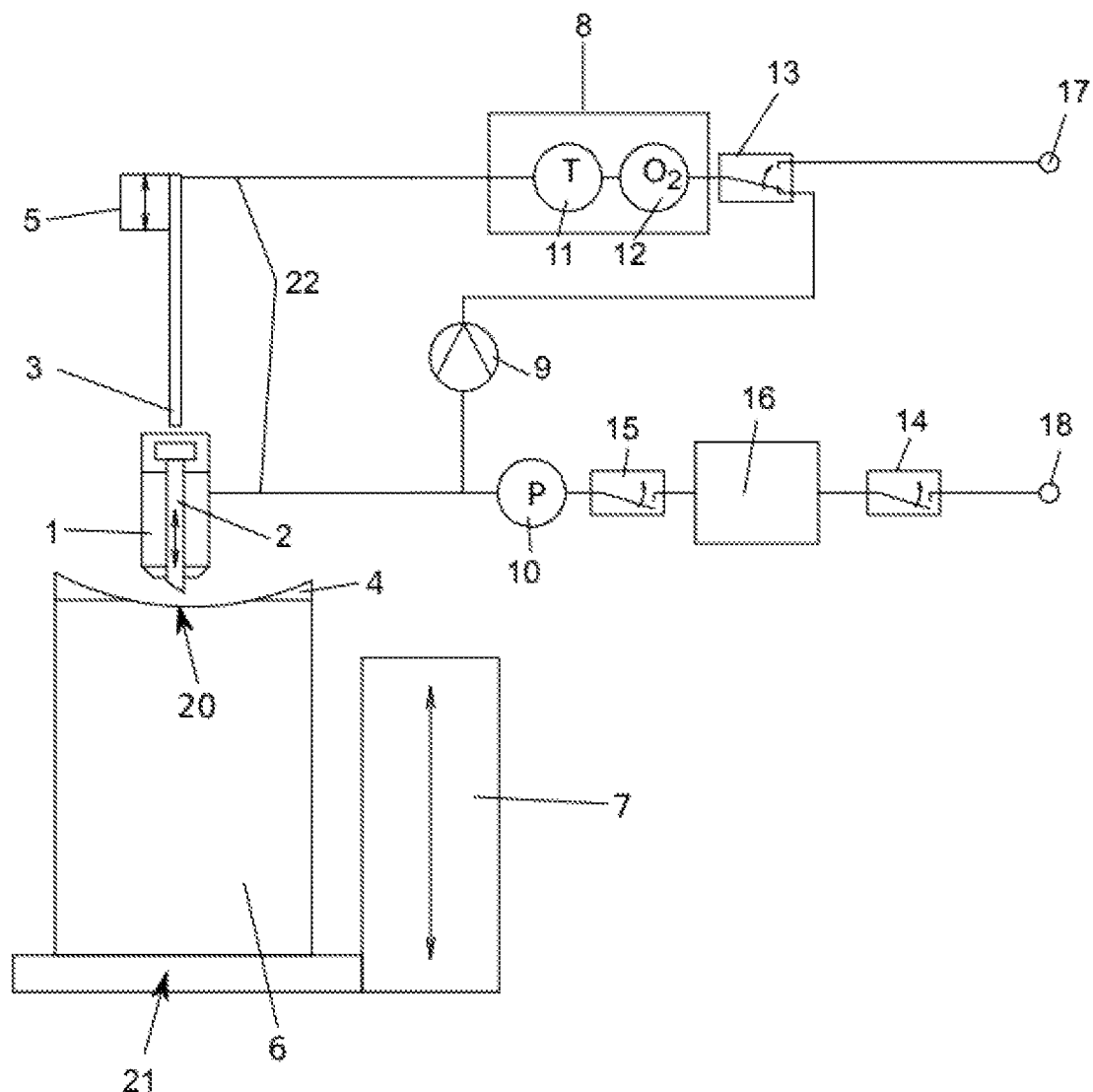

METHOD AND DEVICE FOR MEASURING AN OXYGEN CONTENT OF A HEADSPACE GAS IN A BEVERAGE CAN

CROSS-REFERENCE TO RELATED APPLICATION

This application claims the priority, under 35 U.S.C. § 119, of Austrian patent application AT A50337/2019, filed Apr. 12, 2019; the prior application is herewith incorporated by reference in its entirety.

BACKGROUND OF THE INVENTION

Field of the Invention

The present invention relates to a method for measuring the oxygen content of the headspace gas in a beverage can, in particular a beverage can with a curved bottom. The beverage can is upside down, with the bottom being arranged against gravity, so that the headspace gas collects in the area of the bottom. Using a hollow piercer that is arranged on a piercing head, a sampling opening is introduced in the bottom, in particular in the center of the bottom of the beverage can into which a sampling tube penetrates, and the sampling opening is covered in an airtight manner by means of sealing elements arranged on the piercer or the piercing head. The invention also pertains to a device for carrying out the method.

For beverage fillers, knowledge of the oxygen content in containers such as beverage cans, bottles and the like is of great interest, since said oxygen content influences the shelf life and taste of the beverage and, in the case of metal containers, their corrosion. In order to be able to draw conclusions about the cause of a possibly existing oxygen input, it is important to determine the oxygen content in the liquid and in the gas space above the liquid, the so-called headspace, separately.

In this way it can be determined whether the oxygen has breached the container together with the liquid or through a possibly poorly adjusted filling process. The measurement in the gas space is particularly important because, due to the low solubility of oxygen in aqueous liquids, there is a significant portion of the oxygen of the container in the headspace or the headspace gas. The measurement of the liquid sample is usually a trivial task, since the liquid sample can be sampled from the container via a hose line past an oxygen sensor. In general, there is sufficient sample available to flush past the oxygen sensor until it shows a stable value after an adjustment time. The situation is more difficult when measuring headspace gas. There are usually only a few milliliters of headspace gas, which makes it difficult to flow said headspace gas past the oxygen sensor and discard it.

The situation is particularly difficult when measuring headspace gas, particularly in the case of beverage cans. The first problem is access to headspace gas. The can lid has pre-embossed structures so that the consumer can open the can. Logos and writings are often also embossed, making it very difficult to seal against a measuring apparatus on the can lid and to pierce an access opening. Even if a suitable area is available, the can must be aligned very precisely so that this area is also reliably sealed. The cylindrical can jacket is not mechanically stable enough to seal and pierce there. This leaves only the bottom as a reliably usable place for sealing and piercing. The bottom of $CO_2$-containing beverage cans is always strongly curved inwards, which means that when the can is upside down, the lowest point of the bottom is in the liquid and therefore no access to the headspace can be established. At the same time, the lowest point on the bottom is the point at which one can reliably pierce and seal.

Solutions known from the prior art tilt the can in order to pierce it at the upper edge region or pierce it through the lid, which necessitates precise adjustment of the can and is not possible with all cans. The known methods described require more equipment and more care and training of the operating personnel. For example, Japanese papers JPH04315943 (A) and JP3405637 (B2) disclose devices and methods which open a beverage can at its edge in order to gain access to the headspace gas.

The disadvantage of the prior art methods is that increased accuracy is required when setting and piercing the cans in the sampler. In addition, the sealing of the piercing point in the methods known from the prior art is complicated and often cannot be guaranteed with sufficient certainty to prevent measurement errors due to air or oxygen entering.

SUMMARY OF THE INVENTION

It is accordingly an object of the invention to provide a method and a device, which overcome the above-mentioned and other disadvantages of the heretofore-known devices and methods of this general type and which make it possible to pierce a beverage can at the bottom and then carry out the headspace measurement and which do not require increased requirements in terms of accuracy when setting and piercing the cans in the sampler.

With the above and other objects in view there is provided, in accordance with the invention, a method for measuring an oxygen content of headspace gas in a beverage can, the method comprising:

placing the beverage can upside down, with a bottom of the can being inverted relative to gravity, to enable the headspace gas to collect at the bottom;

using a hollow piercer that is arranged on a piercing head to form a sampling opening in the bottom of the can and causing a sampling tube to penetrate through the sampling opening;

lowering a liquid level in the beverage can by way of the sampling tube to establish a direct connection the headspace that is filled with headspace gas and the sampling opening;

subsequently, after lowering the liquid level, supplying the headspace gas from the headspace of the beverage can to a sensor unit, having a number of sensors, via the sampling tube and/or the hollow piercer or the piercing head, and determining the oxygen content and/or an oxygen partial pressure and/or a headspace volume of the headspace gas by the sensor unit; and covering the sampling opening airtight by sealing elements arranged on the piercer or the piercing head.

In other words, it is provided that the liquid level in the beverage can is lowered via the sampling tube in such a way that there is a direct connection between the headspace that is filled with headspace gas and the sampling opening, wherein, after lowering the liquid level, the headspace gas in the headspace of the beverage can is supplied to a sensor unit comprising a number of sensors, via the sampling tube and/or the hollow piercer or the piercing head, and the oxygen content and/or the oxygen partial pressure and/or the headspace volume of the headspace gas is determined in this way.

By piercing the beverage can at the bottom, it is possible to pierce the sampling opening regardless of a precise positioning and thereby achieve a simple seal. Furthermore, the headspace is made accessible or expanded by lowering the liquid level in order to achieve a simple measurement of the headspace gas.

Particularly advantageous embodiments of the method according to the invention are defined in more detail by the features of the dependent claims:

It can advantageously be provided that the liquid level in the beverage can is lowered by sampling a defined portion of the sample liquid in the beverage can by means of a pump, increasing the pressure by means of a gas that is introduced into the beverage can via the piercer or the sampling tube, in particular nitrogen, or by the pressure prevailing in the beverage can.

The oxygen content of the sample liquid can be easily determined by lowering the sampling tube into the liquid in the beverage can after measuring the oxygen content of the headspace gas and then the liquid is sampled from the beverage can and passed into the sensor unit, and the oxygen content in the liquid is determined in this way.

For simple determination of the oxygen content and/or the oxygen partial pressure and/or the headspace volume, it can be provided that an oxygen sensor is introduced into the headspace created by the lowered liquid level, in particular via the hollow piercer, with which the oxygen concentration or the oxygen partial pressure of the headspace gas is determined.

In an advantageous embodiment it can be provided that, after lowering the liquid level, the headspace gas in the headspace of the beverage can is pumped into the sensor unit, comprising a number of sensors, by means of a pump via the sampling tube and/or the hollow piercer and then back into the headspace of the beverage can and thus the oxygen content and/or the oxygen partial pressure and/or the headspace volume of the headspace gas is determined by the sensor unit. This embodiment ensures that regardless of the headspace gas present, the oxygen content in it can be easily determined and that a plurality of sensors can be used regardless of the free volume in the headspace. Also, there is always enough headspace gas available, since this is recirculated or is pumped back into the headspace, whereby a more precise determination of the oxygen content and/or the oxygen partial pressure and the headspace volume is achieved.

According to the invention it can be provided that for measuring the oxygen content, in particular when measuring beverage cans with foaming liquids, after lowering the liquid level, a foam is generated in the headspace of the beverage can in which the headspace gas or a portion of the headspace gas is bound, the oxygen content and/or the oxygen partial pressure and/or the headspace volume being determined from the foam generated in the sensor unit, in particular the foam subsequently being returned to the headspace of the beverage can. For example, even if only a small portion of the headspace gas is present, the headspace gas bound in the foam or the oxygen contained therein can be easily determined, since due to the poor solubility of oxygen in aqueous substances, the oxygen content in the foam is a very good equivalent of the oxygen content in the headspace.

For simple determination of the oxygen content and/or the oxygen partial pressure and/or the headspace volume, it can be provided that the sensor unit has an oxygen sensor for measuring the oxygen content and/or the oxygen partial pressure of the headspace gas, wherein, in particular, the oxygen content and/or the headspace volume are determined by additional measurement of the pressure by means of a pressure sensor and/or measurement of the temperature by means of a temperature sensor, preferably when a volume change of the headspace gas is brought about.

Since a plurality of sensors are temperature-sensitive or require a temperature adjustment to the medium to be measured in order to achieve maximum accuracy, it can be provided that the headspace gas is pumped from the headspace into the sensor unit, in particular passing the temperature sensor, and then pumped back into the headspace until the sensor unit, in particular the pressure sensor and/or the temperature sensor and/or the oxygen sensor, and/or the headspace gas reach a stable, preferably the same, temperature, and/or sensor-specific adjustment processes have been completed. By repeatedly pumping the headspace gas through the sensor unit, it is achieved that the individual sensors of the sensor unit can accept the temperature of the headspace gas or can be adjusted to this temperature and the measurements of the headspace gas can then be carried out in an adjusted temperature range. Furthermore, the temperature adjustment of the sensors or the sensor unit to the temperature of the headspace gas is accelerated in this way. In addition, other adjustment processes such as, for example, diffusion processes in the oxygen sensor have sufficient time for a complete adjustment.

It can advantageously be provided that the sensor unit has a number of further sensors, in particular a $CO_2$ sensor, an alcohol sensor and/or a sugar sensor, wherein the $CO_2$ content and/or the alcohol content and/or the sugar content of the liquid in the beverage can is determined by means of the further sensors. By arranging different sensors within the sensor unit or within the measuring arrangement, a wide variety of parameters of the sample liquid or the headspace gas can be determined, so that a complete analysis of the sample liquid and/or the headspace gas can be achieved. Alternatively, it can be provided that additional sensors are arranged outside the sensor unit in the line or the ring line.

In order to be able to remove any existing oxygen or impurities from the sample arrangement or to better prevent falsification of the measurement results, before the measurement, it can be provided for the piercer, the piercing head, the sensor unit, the pump, the ring line and/or the sampling tube to be flushed with a flushing medium, in particular nitrogen, and thus are freed from oxygen and/or sample residues.

It can advantageously be provided for the headspace volume to be determined by measuring the pressure in the pierced beverage can first with an inserted and once with a retracted sampling tube, and the headspace volume is calculated using the gas laws and the change in pressure.

It can advantageously be provided that, prior to piercing the container, the pressure in the piercer and/or the piercing head and/or in the ring line, in particular by introduction of nitrogen gas, is adjusted to the internal pressure of the container so that foaming of the sample liquid is prevented. In this way, foam formation can be easily avoided and undesired leakage of the headspace gas can be prevented.

It is a further object of the invention to provide for a device with which the oxygen content of the headspace gas can be easily determined.

With the above and other objects in view there is also provided, in accordance with the invention, a device for measuring the headspace gas in a beverage can.

In other words, according to the invention the device has a line connected to the sampling tube, in particular a ring line, a sensor unit being arranged within the line with which sensor unit the headspace gas of a beverage can can be sampled via the hollow piercer, the device being designed in such a way that the liquid level in the beverage can can be lowered via the sampling tube in such a way that between the headspace that is filled with headspace gas and the sampling opening a direct connection can be established, and wherein the device further comprises a controller which is designed in such a way that the liquid level can be lowered in a defined manner via the piercer or the sampling tube until a direct connection can be established between the headspace that is filled with headspace gas and the sampling opening. With the device according to the invention, the oxygen content or the oxygen partial pressure and/or the headspace volume can be determined easily and a high measuring accuracy is achieved.

In order to be able to simply lower the liquid level, it can be provided that the device comprises means for increasing the pressure in the beverage can, in particular a pump and/or a gas supply device, wherein the device further comprises a controller which is designed in such a way that the liquid level can be lowered in a defined manner.

It can advantageously be provided that the device has a pump and a ring line, wherein the sensor unit is arranged within the ring line with which sensor unit the headspace gas of the beverage can can be sampled via the hollow piercer and can be returned to the headspace of the beverage can via the ring line, in particular via the sampling tube. In this way, even with small amounts of headspace gas, the sensors can be adjusted easily and the measurement accuracy can be increased by pumping over the headspace gas.

It can advantageously be provided that the sensor unit has an oxygen sensor and/or a pressure sensor and/or a temperature sensor and/or a CO2 sensor and/or an alcohol sensor and/or a sugar sensor, the oxygen sensor being designed in particular as an optochemical sensor based on the fluorescence quenching principle or as an electrochemical oxygen sensor.

An effective circulation of the headspace gas can easily be achieved by the pump being designed as a circulation pump, preferably as a diaphragm pump, peristaltic pump, piston pump, gear pump, worm pump, paddle wheel pump or syringe pump.

In order to be able to simply introduce a purge gas, such as, for example, nitrogen, into the device, it can be provided that the device has a number of valves integrated in the ring line, said valves being arranged in the ring line in such a way that the device, in particular the ring line, can be cleaned automatically via said valves.

Other features which are considered as characteristic for the invention are set forth in the appended claims.

Although the invention is illustrated and described herein as embodied in a method and a device for measuring the oxygen content of the headspace gas in a beverage can, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

BRIEF DESCRIPTION OF THE DRAWING

The FIGURE shows a device according to the invention in a schematic representation.

DETAILED DESCRIPTION OF THE INVENTION

Referring now to the sole FIGURE of the drawing in detail there is shown a device according to the invention for determining the oxygen content of the headspace gas of a beverage can in a schematic view. The device comprises a piercing head 1, on which a hollow piercer 2 is arranged. In this embodiment, the piercer 2 is designed like a needle and can be adjusted within piercing head 1 along the double arrow. The device further comprises a sample holder 21, into which a beverage can 6 is inserted. Beverage can 6 is placed upside down on sample holder 21, so that bottom 20 of beverage can 6 points in the direction of piercer 2. Beverage can 6 can be adjusted in the direction of the piercing head 1 by means of a drive 7, as a result of which piercing head 1 can be placed or attached to bottom 20 of sealed beverage can 6. The device further comprises a sampling tube 3, which is arranged concentrically, or coaxially, with the piercer 2 in this embodiment.

Optionally, a centering device or a stop can also be provided, with which the beverage can may be arranged concentrically with piercer 2, so that the center of the bottom of beverage can 6 is aligned with the center of piercer 2.

In the preferred embodiment illustrated in the FIGURE, the piercer 2 is hollow so that sampling tube 3 penetrates piercer 2 and can be brought through said piercer 2 into headspace 4. Sampling tube 3 is adjusted by means of a drive 5. Optionally, it can also be provided that sample holder 21, piercer 2, piercing head 1 and/or sampling tube 3 can be adjusted manually or in a controlled manner by a drive with a controller. At the end of sampling tube 3 which is furthest away from piercing head 1, a ring line 22 begins, which leads back into piercing head 1 or opens into it again. A sensor unit 8 and a pump 9 are integrated in ring line 22. By means of pump 9, a sample liquid located in beverage can 6 or the headspace gas located in headspace 4 of beverage can 6 can be sampled via sampling tube 3 and thus supplied to sensor unit 8. Via sensor unit 8, the sample liquid or the headspace gas is returned through pump 9 into the piercing head and thus back into beverage can 6 or into the headspace 4 of beverage can 6. Optionally, it can also be provided for the headspace gas and/or the sample liquid to be sampled via the piercing head and to be returned through sampling tube 3 into headspace 4 or the sample liquid of beverage can 6.

Optionally, a line can also be arranged on sampling tube 3, piercer 2 or piercing head 1, which line does not open again into the headspace, but rather into the surroundings of the device or a collecting container into which the sampled liquid and/or the headspace gas are drained.

In the embodiment of the FIGURE, sensor unit 8 comprises a temperature sensor 11 and an oxygen sensor 12. The device further comprises a pressure sensor 10 with which the pressure present in ring line 22 or headspace 4 of beverage can 6 can be determined.

It can optionally be provided that the device or sensor unit 8 also comprises a plurality of oxygen sensors 12, which can also be arranged outside the sensor unit.

The method according to the invention is described below by way of example using the embodiment of the FIGURE:

In the method according to the invention, beverage can 6 is placed on sample holder 21 in a first step and then sample holder 21 or piercing head 1 is adjusted so that piercing head 1 is centrally located on bottom 20 of beverage can 6. Subsequently, piercer 2 is adjusted in the direction of the bottom of beverage can 6, pierces it and creates a sampling opening in bottom 20 of beverage can 6. The sampling opening is covered in an airtight manner by means of sealing elements arranged on piercer 2 and/or on piercing head 1, so that no foreign gas can infiltrate the device or ring line 22 or headspace 4 of beverage can 6 and no headspace gas can escape from beverage can 6. The sealing elements of piercing head 1 or piercer 2 thereby seal beverage can 6 and ring line 22 in an airtight manner from the surroundings of the device. Sampling tube 3 is then lowered into can 6. Since in beverage cans 6 there is usually no connection between the headspace and the sampling opening due to the curvature of bottom 20, sampling tube 3 is introduced into the liquid first and part of the liquid is sampled from beverage can 6 until there is a direct connection between the sampling opening and headspace 4 of the beverage can, so that the headspace gas can be supplied to sensor unit 8 or oxygen sensor 12, pressure sensor 10 and temperature sensor 11 via the sampling tube and ring line 22. The sample liquid can be sampled via a valve 13 and opening 17 into the surroundings or a collecting container. Headspace 4 is now freely accessible and can be supplied to an oxygen measurement. As a result of the artificial enlargement of headspace 4, the oxygen mass in headspace 4 remains unchanged, as a result of which the measurement result is not falsified by the lowering of the liquid level. After lowering the liquid level, the enlarged headspace volume can be determined and this can be used to calculate the oxygen mass or the oxygen content in the headspace gas from the measured oxygen partial pressure. The amount of liquid to be sampled depends on beverage can 6 and the nominal filling level and can be determined empirically, for example, by taking a sample for a certain number of seconds and then checking the filling level using the described method.

In an optional embodiment, the headspace volume is measured before the sampling of the liquid and from this headspace volume and the diameter of beverage can 6 it is calculated how much liquid must be sampled in order to determine the access between headspace 4 and the sampling opening. With a known flow rate through sampling tube 3 or the line or ring line 22, the sampling can be time-controlled or can take place via any form of flow measurement.

In the simplest form of the apparatus, the headspace volume can optionally be determined by measuring the pressure in the pierced beverage can once with an inserted sampling tube 3 and once with a retracted sampling tube 3. The additional volume of sampling tube 3 changes the pressure of the headspace gas or the pressure in the beverage can, and the gas laws allow the headspace volume to be calculated if the volume of piercer 2 or sampling tube 3 is known.

A residual fill level, after lowering the liquid level, of approximately 5 mm lower than the lowest point of bottom 20 of beverage can 6 has proven ideal.

After lowering the liquid level, sampling tube 3 is positioned via drive 5 such that it extends into enlarged headspace 4 without being immersed in the liquid. The headspace gas is pumped out of headspace 4 by means of pump 9 and supplied to sensor unit 8 via ring line 22. In sensor unit 8, the oxygen content and the temperature of the headspace gas are determined by means of temperature sensor 11 and oxygen sensor 12. The pressure in headspace 4 is also determined by means of pressure sensor 10 and the volume of the headspace gas is then determined, for example, using the gas equations. The headspace gas is then returned by the pump 9 via ring line 22 from sensor unit 8 via piercing head 1 into headspace 4 of beverage can 6. By circulating the headspace gas via ring line 22, a circulation of the headspace gas within the device is brought about, so that the headspace gas can be pumped past sensor unit 8 or the sensors of the device one or more times. By pumping the headspace gas one or more times past sensor unit 8 or the sensors, a temperature adjustment of the sensors is improved and/or the dependence of the measurement result on the mostly asymptotic adjustment behavior of the sensors, in particular oxygen sensor 12, is reduced, so that the determination of the oxygen content, the oxygen partial pressure and/or the headspace volume is accelerated and the measured value can be determined more precisely. Suitable oxygen sensors from the prior art measure, for example, the oxygen content after diffusion of the oxygen through a membrane, this can necessitate adjustment times for the diffusion of a few seconds, and passivating oxygen layers can also form in front of the respective sensor, which favors a faulty measurement. By pumping the headspace gas one or more times past sensor unit 8 or the sensors, diffusion is improved and likewise it is avoided that passivating oxygen layers are formed.

After determining the oxygen content of the headspace gas or the headspace volume or the oxygen partial pressure, sampling tube 3 can be lowered further from headspace 4 into the sample liquid of the beverage can. The sample liquid is then pumped to sensor unit 8 and the oxygen content, the temperature and the pressure of the sample liquid are also determined.

Alternatively, it can be provided that instead of ring line 22, the device has a line which opens into a collecting container or the like and the sample liquid is sampled in a discarding manner when measuring the oxygen concentration in the liquid past sensor unit 8 and/or when lowering the liquid level.

The liquid level in beverage can 6 can be lowered by means of a pump 9 or by increasing the pressure by means of a gas introduced into beverage can 6 via piercer 2 or sampling tube 3 or piercing head 1. A suitable gas is any gas that does not change the oxygen concentration in beverage can 6, such as, for example, nitrogen. Alternatively, the liquid level can be lowered by means of the pressure prevailing in the beverage can, this is provided in particular for beverage cans 6 with carbonated drinks.

The problem is that beverage cans 6 with foaming liquids, for example beer, tend to foam after piercing and lowering the liquid level by means of piercer 2, in particular when inserted quickly into sample holder 21. In the resulting foam, part of the headspace gas is locally bound almost stationary, so that this bound gas portion is not involved in the measuring process via ring line 22. Optionally, in the case of foaming liquids foam can be deliberately generated or foam formation can be promoted so that the entire headspace gas is bound homogeneously in the foam. The foam formation can take place, for example, by positioning sampling tube 3 via drive 5 a few millimeters below the liquid surface and pumping the headspace gas from piercing head 2 via pump 9 and sampling tube 3 into the liquid surface and producing foam there. The foam generated can then be supplied to sensor unit 8 by means of pump 9 via ring lines 22 and the oxygen content of the foam can thus be determined. Since the oxygen content of the foam corresponds to that of headspace 4 or the headspace gas due to the poor solubility of oxygen in the sample liquid, the oxygen content of the headspace gas can thus be determined.

The correct setting of the gas pressure in piercer 2 when piercing bottom 20 of beverage can 6 differs depending on the beverage can and the sample liquid contained therein. Especially in the case of samples that tend to form a stiff foam, usually at low temperatures, the pressure of the gas in piercer 2 must be matched to the liquid. Namely, if the piercer pressure or the pressure of piercer 2 is chosen to be significantly higher than the internal pressure of beverage can 6, then, when pierced, nitrogen shoots through the liquid into the headspace, thereby forming foam which immobilizes the oxygen in the headspace and makes it unavailable for the measurement that follows. The pressure in piercer 2 is therefore preferably lower than the can internal pressure. Only when enough liquid has been sampled so that the headspace is accessible through the pierced opening, the pressure can be increased via valves 14, 15 and storage volume 16 or pump 9, thus further lowering the liquid level or sampling the headspace gas.

Since the sensors usually have an asymptotic adjustment behavior with a sensor-specific adjustment time and a temperature-dependent measurement behavior, it is advantageous that the sensors, in particular oxygen sensor 12 and temperature sensor 11, are adjusted to the temperature or concentration of the headspace gas or the sample liquid. In order to be able to carry out this adjustment quickly, headspace gas 4 is optionally pumped past sensor unit 8 or the sensors several times, thus accelerating the adjustment. By circulating the headspace gas or by repeatedly pumping the headspace gas, even small amounts of the headspace gas can be measured by means of sensor unit 8, or a rapid adjustment of the sensors to the headspace gas and the sample liquid can be achieved even with small amounts of the headspace gas. This adjustment can include all time-dependent effects such as the temperature adjustment and/or the diffusion of the measurement gas through the membrane of the sensor, etc.

The device further comprises a valve 13 arranged in ring line 22, which is connected to a line leading into the surroundings at an opening 17. Via opening 17, for example, a flushing gas such as nitrogen or a cleaning solution can get into the ring line or to sensor unit 8 or pump 9 and the sensors and thus sample residues or residual oxygen can be flushed out of the device.

Optionally, it can be provided that, as shown in the FIGURE, the device comprises a number of further valves 14, 15 and a storage volume 16. Storage volume 16 is connected to pressure sensor 10 via valve 15 and connected to the surroundings of the device via a further valve 14. Since the headspace gas originally located only in headspace 4 can be distributed in ring line 22 when beverage can 6 is opened or after the liquid level is lowered by piercer 2, lower $O_2$ concentrations are measured than were present in headspace 4 of originally closed beverage can 6. This systematic error is corrected by calculation. To this end, the pump circuit volume or the volume of ring lines 22 and the components connected thereto and the headspace volume must be known. The headspace volume is determined in the course of the measurement process by sensor unit 8 or pressure sensor 10 and temperature sensor 11 and/or determined by using the gas laws.

For this purpose, an empty storage volume 16 is integrated in the device of the embodiment of the FIGURE. In a first step before beverage can 6 is pierced, valve 14, which is connected to the surroundings of the device via an air inlet 18, is opened and storage volume 16 is brought to ambient air pressure. If valve 15, which connects the storage volume to ring line 22, is open, a first air pressure p2 can be measured. Now valves 14 and 15 are closed. After piercing beverage can 6 by piercer 2, pressure p1 is measured, which results from the combination of the pressure of pierced beverage can 6 and the pressure applied in piercing head 1 and ring lines 22. Then, valve 15 is opened and the resulting mixing pressure p3 is measured. If the storage volume 16 is known, the headspace volume $V_{Headspace}$ can now be calculated using Boyle Mariotte's law (equation 1).

$$V_{Headspace} = V_{Expansion} \times \frac{Pa - P2}{P1 - Pa} - V_{apparatus} \qquad \text{Equation 1}$$

Since the expansion is neither purely isothermal nor purely adiabatic, the result is only a good approximation.

The expansion volume $V_{Expansion}$ and the apparatus volume $V_{Apparatus}$, i.e., the volume in the device or in ring line 22, sampling tube 3, piercer 2 and piercing head 1, can be determined from the design, however, it is better if various known headspace volumes $V_{Headspace}$ are used to carry out a series of measurements and, based on those measurements, $V_{Expansion}$ and $V_{Apparatus}$ are calculated. In addition to the known structural geometry information, the two values then also contain corrections for deviations from the isothermal behavior and can thus enable an even more precise result of the measurement.

The measured oxygen concentration can then be corrected using the known volumes using equation 2.

$$O_{2,corr} = O_{2,measured} \times \frac{V_{Apparat} + V_{Headspace}}{V_{Headspace}} \qquad \text{Equation 2}$$

Alternatively, at the start of the measurement, storage volume 16 can also be brought to a higher pressure than that prevailing in beverage can 6. For this purpose, piercing head 1 is sealed with piercer 2 to beverage can 6 before piercing. Then, valves 14 and 15 are opened so that the same pressure prevails in the entire area between air inlet 18 and piercing head 1. This pressure is measured with pressure sensor 10. Valves 14 and 15 are then closed and the pressure is thus "locked in" in storage volume 16. The remaining method for measuring the oxygen concentration is then carried out analogously to the method described above.

Alternatively, it can be provided that the headspace gas or the sample liquid is pumped into ring line 22 out via piercer 2 or sampling tube 3 connects directly to piercer 2. Alternatively, after opening or piercing bottom 20 of beverage can 6, piercer 2 can remain in headspace 4 and the headspace gas or the sample liquid can be pumped into ring line 22 or the liquid level can be lowered via piercer 2.

Optionally, sensor unit 8 or the device can also have a number of further sensors, for example a $CO_2$ sensor, an alcohol sensor, a sugar sensor and/or further sensors, which are integrated in ring line 22 or sensor unit 8. The further sensors can be used, for example, to determine the $CO_2$ content or the alcohol content or the sugar content of the sample liquid and thus determine further parameters of the sample liquid. The further sensors can optionally also be filled with the sample liquid via opening 17. The further sensors can, for example, provide further information during the production of beverages such as beer or lemonades, so that the quality control of the filling process or of the production process can be easily monitored by means of the device according to the invention.

Oxygen sensor 12 can in particular be designed as an optochemical sensor based on the fluorescence quenching principle or, for example, as an electrochemical oxygen sensor. Optionally to the embodiment shown in the FIGURE, the sensor unit can also comprise only one oxygen sensor 12, with which the oxygen content of the headspace gas and/or the sample liquid is determined.

Pump 9 of the embodiment shown in the FIGURE can be designed, for example, as a circulation pump, in particular as a diaphragm pump, peristaltic pump, piston pump, gear pump, worm pump, paddle wheel pump or syringe pump.

Optionally, drive 7 or the adjustment mechanisms of piercer 2 and sampling tube 3 can be driven manually or in a different manner, thus causing the individual parts to be displaced relative to one another.

The invention claimed is:

1. A method for measuring an oxygen content of headspace gas in a liquid-filled beverage can, the method comprising:
    placing the beverage can upside down, with a bottom of the can being inverted relative to gravity, to enable the headspace gas to collect at the bottom;
    using a hollow piercer that is arranged on a piercing head to form a sampling opening in the bottom of the can and causing a sampling tube to penetrate through the sampling opening;
    lowering a liquid level of a liquid in the beverage can by way of the sampling tube to establish a direct connection of a headspace that is filled with headspace gas and the sampling opening;
    subsequently, after lowering the liquid level, supplying the headspace gas from the headspace of the beverage can to a sensor unit, having a number of sensors, via the sampling tube and/or the hollow piercer or the piercing head, and determining the oxygen content and/or an oxygen partial pressure and/or a headspace volume of the headspace gas by the sensor unit; and
    covering the sampling opening airtight by sealing elements arranged on the piercer or the piercing head.

2. The method according to claim 1, wherein the beverage can has a curved bottom, and the sampling opening is formed in a center of the bottom of the beverage can.

3. The method according to claim 1, which comprises lowering the liquid level in the beverage can by sampling a defined portion of the liquid in the beverage can by way of a pump, increasing a pressure by introducing a gas into the beverage can via the piercer or the sampling tube, or by a pressure prevailing in the beverage can.

4. The method according to claim 1, which comprises, after a measurement of the oxygen content of the headspace gas, lowering the sampling tube into the liquid in the beverage can and then sampling the liquid from the beverage can and passing into the sensor unit and thus determining an oxygen content in the liquid.

5. The method according to claim 1, wherein in the headspace created by the lowered liquid level, an oxygen sensor is introduced, with which tie an oxygen concentration or the oxygen partial pressure of the headspace gas is determined.

6. The method according to claim 1, wherein, after lowering the liquid level, the headspace gas in the headspace of the beverage can is pumped into the sensor unit having the number of sensors, by means of a pump via the sampling tube and/or the hollow piercer and then back into the headspace of the beverage can and thus determining with the sensor unit the oxygen content and/or the oxygen partial pressure and/or the headspace volume of the headspace gas.

7. The method according to claim 6, wherein the headspace gas is pumped from the headspace into the sensor unit, passing a temperature sensor of the sensor unit, and then pumped back into the headspace until a pressure sensor of the sensor unit and/or a temperature sensor of the sensor unit and/or an oxygen sensor of the sensor unit, and/or the headspace gas reach a stable temperature, and/or sensor-specific adjustment processes have been completed.

8. The method according to claim 1, wherein the beverage can contains a foaming liquid, and the method further comprises, after lowering the liquid level, generating a foam in the headspace of the beverage can in which the headspace gas or a portion of the headspace gas is bound, and determining the oxygen content and/or the oxygen partial pressure and/or the headspace volume from the foam generated in the sensor unit, and, optionally, subsequently returning the foam to the headspace of the beverage can.

9. The method according to claim 1, wherein the sensor unit has an oxygen sensor for measuring the oxygen content and/or the oxygen partial pressure of the headspace gas, wherein the oxygen content and/or the headspace volume are determined by additional measurement of a pressure by means of a pressure sensor of the sensor unit and/or measurement of a temperature by means of a temperature sensor of the sensor unit.

10. The method according to claim 9, which comprises determining the oxygen content and/or the headspace volume by additional measurement of the pressure with the pressure sensor and/or measurement of the temperature with the temperature sensor when a volume change of the headspace gas is brought about.

11. The method according to claim 1, wherein the sensor unit includes sensors selected from the group consisting of a $CO_2$ sensor, an alcohol sensor, and a sugar sensor, and the sensors are configured to determine a $CO_2$ content and/or an alcohol content and/or a sugar content of the liquid in the beverage can.

12. The method according to claim 1, which comprises, before determining an oxygen content of headspace gas, flushing one or more device elements selected from the group consisting of the piercer, the piercing head, the sensor unit, a pump, a ring line, and the sampling tube with a flushing medium to thus free the device elements from oxygen and/or sample residues.

13. The method according to claim 1, wherein the headspace volume is determined by measuring a pressure in the pierced beverage can first with an inserted and once with a retracted sampling tube, and the headspace volume is calculated using gas laws and a change in pressure.

14. The method according to claim 1, wherein, prior to piercing the beverage can, a pressure in the piercer and/or the piercing head and/or in a ring line, is adjusted to an internal pressure of the beverage can to prevent foaming of the liquid in the beverage can.

15. A device for determining an oxygen content of a headspace gas in a liquid-filled beverage can inverted relative to gravity, the device comprising:
    a piercing head having disposed thereon a hollow piercer and a sampling tube, wherein the hollow piercer is configured to form a sampling opening in a bottom of the inverted beverage can and the sampling tube is configured to penetrate through the sampling opening;
    a line connected to said sampling tube;
    a sensor unit arranged within the line and configured to sample the headspace gas of the inverted beverage can via the hollow piercer;
    said sampling tube is configured to enable a liquid level in the beverage can to be lowered via the sampling tube such that a direct connection between a headspace that is filled with headspace gas at the bottom of the can and the sampling opening is established; and a controller configured to cause the liquid level in the inverted beverage can to be lowered in a defined manner via the piercer until a direct connection is established between the headspace that is filled with the headspace gas and the sampling opening.

16. The device according to claim 15, configured to perform the method according to claim 1.

17. The device according to claim 15, further comprising a pump and a ring line, wherein said sensor unit is arranged within said ring line with which sensor unit the headspace gas of the beverage can is sampled via the hollow piercer and is returned to the headspace of the beverage can via the ring line and the sampling tube.

18. The device according to claim 17, wherein said pump is a circulation pump selected from the group consisting of a diaphragm pump, a peristaltic pump, a piston pump, a gear pump, a worm pump, a paddle wheel pump, and a syringe pump.

19. The device according to claim 15, wherein said sensor unit has an oxygen sensor and/or a pressure sensor and/or a temperature sensor and/or a $CO_2$ sensor and/or an alcohol sensor and/or a sugar sensor, the oxygen sensor being an optochemical sensor based on a fluorescence quenching principle or being an electrochemical oxygen sensor.

20. The device according to claim 15, wherein said line is a ring line having a plurality of valves integrated therein, said valves being arranged in the ring line in such a way that the device is cleaned automatically via the valves.

* * * * *